United States Patent [19]

Betz et al.

[11] Patent Number: 4,970,321
[45] Date of Patent: Nov. 13, 1990

[54] PREPARATION OF CYCLIC N,N'-DIMETHYLUREAS

[75] Inventors: Rainer Betz, Ludwigshaften; Erwin Hahn, Heidelberg; Rolf Fikentscher, Ludwigshaften, all of Fed. Rep. of Germany

[73] Assignee: BASF Aktiengesellshaft, Ludwigshaften, Fed. Rep. of Germany

[21] Appl. No.: 397,878

[22] Filed: Aug. 23, 1989

[30] Foreign Application Priority Data

Sep. 2, 1988 [DE] Fed. Rep. of Germany ....... 3829848

[51] Int. Cl.$^5$ ................... C07D 233/30; C07D 239/02
[52] U.S. Cl. ..................................... 548/317; 544/315
[58] Field of Search ................ 548/301, 317; 544/315; 540/485, 450

[56] References Cited

FOREIGN PATENT DOCUMENTS 215964 4/1987 European Pat. Off. ............ 548/301
222664 5/1987 European Pat. Off. ............ 548/301
249136 12/1987 European Pat. Off. ............ 548/301

OTHER PUBLICATIONS

Journal of Chemical and Engineering Data, vol. 21, No. 2, 1976, pp. 150-153, J. Rosenfarb et al., "Dielectric Constants, Viscosities, and Related Physical Properties of Several Substituted Liquid Ureas at Various Temperatures".
Journal of Organometallic Chemistry, vol. 117, 1976, pp. 149-155, Hideki Sakurai et al., "Chemistry of Organosilicon Compounds", (with English translation).
Angew. Chem., vol. 82, 1970, pp. 73-77, (no English translation).

*Primary Examiner*—Mary C. Lee
*Assistant Examiner*—Robert C. Whittenbaugh
*Attorney, Agent, or Firm*—Oblon, Spivak, McClelland, Maier & Neustadt

[57] ABSTRACT

Cyclic N,N'-dimethylureas I

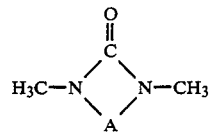

where A is a 1,2- or 1,3-alkylene group of 2 to 10 carbon atoms, are prepared by reacting the corresponding non-methylated cyclic urea with formaldehyde and excess formic acid and then removing the formic acid still present in the reaction mixture, by a process in which the formic acid is subjected to a thermal decomposition reaction by means of a catalyst system consisting of a tertiary amine and a copper salt.

8 Claims, No Drawings

PREPARATION OF CYCLIC N,N'-DIMETHYLUREAS

The present invention relates to an improved process for the preparation of cyclic N,N'-dimethylureas of the general formula I

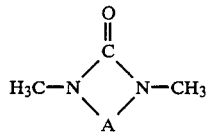

where A is a 1,2- or 1,3-alkylene group of 2 to 10 carbon atoms, by reacting a cyclic urea of the general formula II

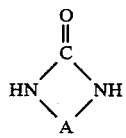

with formaldehyde and excess formic acid and then removing the formic acid still present in the reaction mixture.

A large number of syntheses have been described in the literature for the cyclic N,N,-dimethylureas I, which are used, for example, as special solvents, and in particular for the two most important members of this class of substances, ie. N,N'-dimethyl-1,2-ethyleneurea (DMEU) and N,N'-dimethyl-1,3-propyleneurea (DMPU).

For example, the preparation of DMEU and DMPU by reacting the corresponding cyclic ureas II with formaldehyde and excess formic acid is described in Journal of Chemical and Engineering Data, 21. No. 2 (1976), 150 (1) and Journal of Organometallic Chemistry, 117 (1976), 153 (2). The difficulty in working up the reaction mixtures is associated with the removal of the formic acid still present. Because of the high polarity of the methylated ureas I, the formic acid, which is also strongly polar, cannot be separated from I by distillation. Thus, (1) describes the neutralization of the formic acid with NaOH to give nonvolatile sodium formate and subsequent distillation of I. In (2), I is converted with HCl into the nonvolatile hydrochloride, after which the formic acid is evaporated, the residue is converted by means of NaOH back into the free methylated urea I and the latter is isolated by extraction and distillation. Both are very involved working up methods, especially since in (1) the resulting product has to be further purified by other purification steps.

Angew. Chem. 82 (1970), 73–77 (3) discloses 3:1 and 2:1 adducts of formic acid with tertiary amines (III). These compounds, as isolated pure substances, decompose thermally in the presence of, for example, copper(I) chloride to give the amines III and the gaseous products CO, $CO_2$, $H_2$ and/or $H_2O$.

It is an object of the present invention to overcome the disadvantages described in the preparation of I from II, formaldehyde and formic acid.

We have found that this object is achieved by a process for the preparation of cyclic N,N'-dimethylureas I

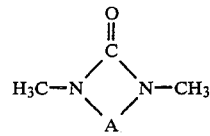

where A is a 1,2- or 1,3-alkylene group of 2.to 10 carbon atoms, by reacting a cyclic urea II

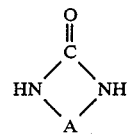

with formaldehyde and excess formic acid and then removing the formic acid still present in the reaction mixture, wherein the formic acid is subjected to a thermal decomposition reaction by means of a catalyst system consisting of a tertiary amine (III) and a copper salt.

The reductive alkylation of the cyclic ureas II presumably takes place via the stage of intermediate N-methylol compounds by reaction of II with formaldehyde. The formic acid is required both as a reducing agent for the methylol derivatives and as a solvent for the total reaction. The excess of formic acid is usually from 5 to 10, preferably from 5 to 7, times the molar amount of II. The formic acid used may also contain up to 20% by weight of water.

Formaldehyde is used, as a rule, as a 30–50% strength by weight aqueous solution. However, substances which release formaldehyde under the reaction conditions, such as paraformaldehyde or trioxane, can also be used. The formaldehyde is generally used in the stoichiometric amount (2 moles per mole of II) or, preferably, in slight excess, for example in up to three times the molar amount, based on II.

The reaction of the cyclic ureas II with formaldehyde and formic acid is usually carried out at temperatures close to the boiling point of the formic acid (101° C.), preferably at from 80° to 110° C. The reaction time is, as a rule, from 12 to 20 hours.

In a preferred embodiment of the novel process, some of the formic acid still present in the reaction mixture after the reaction is distilled off together with water, the distillation being carried out under reduced pressure or, preferably, atmospheric pressure, after which the remaining amount is subjected to the thermal decomposition reaction. The residual amount of formic acid in the distillation residue is usually from 10 to 30% of the amount used for the reaction. If temperatures below about 115° C. are employed, the catalyst system consisting of the amine III and the copper salt can be added at any time during the process prior to the decomposition reaction of the formic acid, because the catalyst system only becomes effective at the temperatures of the decomposition reaction. After the decomposition reaction, the product I is isolated by distillation.

In another preferred embodiment of the novel process, a formic acid/water mixture is first distilled off under reduced pressure or, preferably, atmospheric pressure and then a mixture of formic acid and the product I is distilled off under reduced pressure, preferably from 5 to 100, in particular from 10 to 50, mbar. Thereafter, the formic acid/I mixture distilled off, which generally still contains from 10 to 30% of the amount of formic acid used for the reaction, is mixed with the catalyst system consisting of the amine III and the copper salt and is subjected to the thermal decomposition reaction. After the decomposition reaction, the product I is isolated by distillation.

Suitable catalysts for the decomposition of adducts formed as intermediates from formic acid and tertiary amine (III) are copper salts, preferably copper(I) halides, in particular copper(I) chloride. The copper salts are preferably used in an amount from 0.1 to 5, in particular from 0.5 to 2, mol % per mole of the formic acid to be decomposed.

Examples of tertiary amines (III) are the amines mentioned in (3). Trialkylamines whose alkyl groups may be identical or different and are each of 1 to 4 carbon atoms are preferred. Examples of trialkylamines are trimethylamine, triethylamine, tri-n-propylamine, triisopropylamine, tri-n-butylamine, triisobutylamine, tri-secbutylamine, tri-tert-butylamine, dimethylethylamine, diethylmethylamine, diisopropylmethylamine and diisopropylethylamine. Triethylamine is particularly preferred. However, cyclic amines, such as N-methylpiperidine, N-methylpyrrolidine, N-methylmorpholine and 1,4-diazabicyclo[2.2.2]octane, and araliphatic amines, such as N,N-dimethylbenzylamine, can also be used. It is also possible to use mixtures of the stated amines. The tertiary amines (III) are preferably used in an amount of from 0.1 to 5, in particular from 0.5 to 2, mol % per mole of the formic acid to be decomposed.

The thermal decomposition reaction of the formic acid takes place with the novel catalyst system at from 120° to 250° C., preferably from 140° to 200° C., in particular from 150° to 170° C. The onset of the decomposition reaction is evident from vigorous evolution of gas. The duration of the decomposition reaction is usually from 4 to 10 hours.

The novel process can advantageously be used for the preparation of the dimethylureas I having a 5-membered or 6-membered ring. Examples of I are: N,N'-dimethyl-1,2-ethyleneurea(DMEU),N,N,-dimethyl-1,2-propyleneurea, N,N'-dimethyl-1,3-propyleneurea (DMPU), N,N'-dimethyl-1,2-butyleneurea, N,N'-dimethyl-1,3-butyleneurea, N,N'-dimethyl-1,3-butyleneurea, 4,5-diethyl-1,3-dimethyl-2-imidazolidinone and 4,6-diethyl-1,3-dimethyl-3,4,5,6-tetrahydro-2(1H)-pyrimidinone. The process is particularly important for the preparation of DMEU and DMPU.

The novel process is a simple and effective method for removing formic acid from the reaction mixtures in the conversion of the cyclic ureas II into the methylated compounds I. In particular, there are no losses of yield as a result of working up comprising a large number of involved steps, as described in (1) or (2). The yields in the novel process are thus substantially higher.

EXAMPLE 1

Preparation of N,N'-dimethyl-1,3-propyleneurea (DMPU)

A mixture of 400g (4.0 moles) of 1,3-propyleneurea, 920 g (20 moles) of formic acid (98-100% by weight), 576 g of a 50% strength by weight aqueous formaldehyde solution 6 moles of formaldehyde, 4.0 g (40 millimoles) of triethylamine and 4.0 g (40 millimoles) of copper(I) chloride was refluxed for 16 hours. Thereafter, formic acid was distilled off under atmospheric pressure together with water until the distillation residue had reached 150° C. The amount of formic acid remaining in the residue was 160 g (3.5 moles). Above 150° C., vigorous evolution of gas began. Stirring was carried out for from 5 to 10 hours at this temperature, after which the acid number of the reaction mixture decreased to less than 1 mg of KOH/mg. The product was isolated by distillation under 60 mbar at a boiling point of 144 146° C. and was sufficiently pure. The yield of DMPU was 94%.

EXAMPLE 2

Preparation of N,N,-dimethyl-1,2-ethyleneurea (DMEU)

A mixture of 344 g (4.0 moles) of 1,2-ethyleneurea, 920 g (20 moles) of formic acid (98-100% by weight) and 576 g of a 50% strength by weight aqueous formaldehyde solution 9.6 moles of formaldehyde) was refluxed for 16 hours. Thereafter, formic acid was distilled off under atmospheric pressure together with water until the distillation residue had reached 150° C. The product was then distilled over under 50 mbar together with 160 g (3.5 moles) of remaining formic acid. 4.0 g (40 millimoles) of triethylamine and 4.0 g (40 millimoles) of copper(I) chloride were added to this distillate, and the mixture was stirred at 150° C. for from 4 to 6 hours with vigorous evolution of gas, after which the acid number of the mixture decreased to less than 1 mg of KOH/g. The product was isolated by distillation under 23 mbar and at a boiling point of 106°-108° C. and was sufficiently pure. The yield of DMEU was 80%.

We claim:

1. A process for the preparation of a cyclic N,N'dimethylurea of the formula I

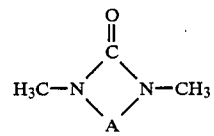

where A is a 1,2- or 1,3-alkylene group of 2 to 10 carbon atoms, by reacting a cyclic urea of the formula II

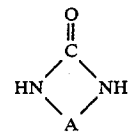

with formaldehyde and excess formic acid and then removing the formic acid still present in the reaction mixture, wherein the formic acid is subjected to a thermal decomposition reaction by means of a catalyst system consisting of a tertiary amine (III) and a copper salt.

2. A process as claimed in claim 1, wherein some of the formic acid still present in the reaction mixture after the reaction is distilled off and the remaining amount is subjected to the decomposition reaction.

3. A process as claimed in claim 1, wherein, after the end of the reaction, the product I formed is distilled off together with formic acid still present, and the formic acid in the distillate is subjected to the decomposition reaction.

4. A process as claimed in claim 1, wherein the copper salt used is copper(I) chloride.

5. A process as claimed in claim 1, wherein the tertiary amine (III) used is a trialkylamine whose alkyl groups may be identical or different and are each of 1 to 4 carbon atoms.

6. A process as claimed in claim 1, wherein the tertiary amine (III) and the copper salt are each used in an amount of from 0.1 to 5 mol % per mole of the formic acid to be decomposed.

7. A process as claimed in claim 1, wherein the decomposition reaction is carried out at from 120 to 250° C.

8. A process as claimed in claim 1, which is used for the preparation of N,N'-dimethyl-1,2-ethyleneurea or N,N'-dimethyl-1,3-propyleneurea.

* * * * *